(12) United States Patent
Shimase et al.

(10) Patent No.: US 10,266,801 B2
(45) Date of Patent: Apr. 23, 2019

(54) CELL CULTURE DEVICE

(71) Applicant: Hitachi High-Technologies Corporation, Tokyo (JP)

(72) Inventors: Akihiro Shimase, Tokyo (JP); Kazumichi Imai, Tokyo (JP); Eiichiro Takada, Tokyo (JP); Sadamitsu Aso, Tokyo (JP)

(73) Assignee: Hitachi High-Technologies Corporation, Tokyo (JP)

( * ) Notice: Subject to any disclaimer, the term of this patent is extended or adjusted under 35 U.S.C. 154(b) by 17 days.

(21) Appl. No.: 15/106,945

(22) PCT Filed: Dec. 24, 2014

(86) PCT No.: PCT/JP2014/084016
§ 371 (c)(1),
(2) Date: Jun. 21, 2016

(87) PCT Pub. No.: WO2015/111348
PCT Pub. Date: Jul. 30, 2015

(65) Prior Publication Data
US 2017/0037351 A1    Feb. 9, 2017

(30) Foreign Application Priority Data
Jan. 27, 2014  (JP) ................... 2014-012072

(51) Int. Cl.
*C12M 1/00* (2006.01)
*C12M 3/06* (2006.01)

(52) U.S. Cl.
CPC ............ *C12M 23/40* (2013.01); *C12M 23/50* (2013.01); *C12M 27/16* (2013.01); *C12M 29/00* (2013.01)

(58) Field of Classification Search
CPC ............................ C12M 23/40; C12M 23/50
(Continued)

(56) References Cited

U.S. PATENT DOCUMENTS

2009/0137026 A1    5/2009  Kobayashi et al.
2010/0216229 A1*   8/2010  Kenney .................. C12M 23/08
                                                        435/303.1

(Continued)

FOREIGN PATENT DOCUMENTS

JP    2009-125027 A    6/2009
JP    2011-142837 A    7/2011

OTHER PUBLICATIONS

International Search Report of PCT/JP2014/084016 dated Apr. 7, 2015.

*Primary Examiner* — Kevin Joyner
*Assistant Examiner* — Holly M Mull
(74) *Attorney, Agent, or Firm* — Mattingly & Malur, PC (57) ABSTRACT

According to the present invention, a simple structure can be used to achieve reliable liquid delivery with no residual air, and simple attachment/detachment of a culture vessel, and thus a closed-system cell culture device exhibiting high reliability can be constructed at low cost. In the present invention, a liquid is supplied or discharged while a culture vessel is in an inclined state. The culture vessel is provided with two flow paths, namely an intake flow path and a discharge flow path, which connect a culture chamber and a connection member. Points where the flow paths join with the culture chamber are respectively configured as an intake port and a discharge port. The discharge port is provided in the position nearest to the axis of inclination of the culture vessel. The intake port is provided in a plane projected from a vertical plane including the aforementioned axis of inclination.

20 Claims, 5 Drawing Sheets (58) Field of Classification Search
USPC .................................................... 435/289.1
See application file for complete search history.

(56) References Cited

U.S. PATENT DOCUMENTS

| | | | | |
|---|---|---|---|---|
| 2011/0249526 | A1* | 10/2011 | Wong | B01F 7/162 366/142 |
| 2011/0310696 | A1* | 12/2011 | Goodwin | B01F 7/00691 366/204 |
| 2014/0011269 | A1* | 1/2014 | Sakura | C12M 21/06 435/289.1 |
| 2015/0138913 | A1* | 5/2015 | Jones | B01F 7/001 366/185 |
| 2015/0166945 | A1* | 6/2015 | Andersen | C12M 21/16 435/305.1 |
| 2015/0218503 | A1* | 8/2015 | Kiyama | C12M 23/10 435/297.1 |
| 2016/0186124 | A1* | 6/2016 | Jager | C12M 23/40 435/289.1 |

\* cited by examiner

CELL CULTURE DEVICE

TECHNICAL FIELD

The present invention relates to a cell culture device for culturing cells using a culture vessel.

BACKGROUND ART

Processes in the cultivation of cells have been conducted by a skilled operator manually in a clean room which is sterilized as much as possible by strict production steps. Therefore, large-scale cell cultivation requires enormous cost of manpower and considerable cost of equipment, which have been enormous obstacles to industrialization.

It is possible to automate a series of manual culture operations using a robot and to reduce the cost of manpower. However, because the culture operations include operations in which the inside of the culture vessel is opened, such as the change of the culture medium in which the cover of the culture vessel is opened, the risk of contamination from the outside cannot be eliminated. Therefore, the whole system including the robot has to be placed in a large-scale clean room, and it is difficult to reduce the cost of equipment considerably.

Accordingly, systems for culturing cells in which a closed system is formed by connecting a liquid bag containing a culture medium, a culture vessel, a liquid waste bag and the like (hereinafter referred to as a closed culture system) and in which the change of the culture medium and the like are conducted in the system have been invented. An example of the systems is described in JP-A-2011-142837 (PTL 1). Because the risk of contamination from the outside can be eliminated with such a system, keeping the cleanliness of the installation location of the system at the minimum level is sufficient, and the cost of equipment can be reduced considerably.

On the other hand, a closed culture system is restricted in the handling of liquid delivery; for example, a liquid should be sent by a liquid-driving force from the outside of the system. Therefore, the handling requires ingenuity. For example, when a liquid is sent to the culture vessel, it is necessary to send the liquid with ingenuity so that air does not remain in the culture vessel. JP-A-2009-125027 (PTL 2) describes an example in which the inlet port and the discharge port of the culture vessel are spaced and the culture vessel is inclined vertically when a liquid is sent.

CITATION LIST

Patent Literature

PTL 1: JP-A-2011-142837
PTL 2: JP-A-2009-125027

SUMMARY OF INVENTION

Technical Problem

When tubes from a liquid bag and a liquid waste bag are connected to an intake flow path and a discharge flow path of a culture vessel, it is more convenient to gather the flow paths at the culture vessel side and gather the tubes at the side of the bags so that the flow paths and the tubes are in the form of single flow path sockets, which are then connected to each other, than separately connecting the tubes to the respective flow paths. This is because only one connection is required. In the culture vessel described in PTL 2, however, the intake flow path and the discharge flow path are joined with the culture vessel from the opposite sides of the culture plane. Thus, to connect the tubes to the flow paths in the form of flow path socket, the direction of a flow path should be changed for example by folding back one of the flow paths. In this case, the shape of the flow path becomes complex, which causes a problem of an increase in the cost of the culture vessel.

Solution to Problem

In order to solve the above problems, the cell culture device of the invention has a culture vessel, a connection member connected to the culture vessel, an inclining mechanism for inclining the connection member and a driving mechanism for supplying a fluid to the culture vessel. In the cell culture device, a liquid is supplied to the culture vessel while the inclining mechanism inclines the connection member with the culture vessel; a gas is supplied to the culture vessel while the inclining mechanism inclines the connection member with the culture vessel to the opposite side to the side of inclination for supplying the liquid to discharge a liquid from the culture vessel; the culture vessel has a culture chamber and two flow paths, namely an intake flow path and a discharge flow path, which join the culture chamber and the connection member; the points where the culture chamber joins with the two flow paths are respectively configured as an intake port and a discharge port; the discharge port is provided in a position nearest to an axis of inclination caused by the inclining mechanism; and the intake port is provided in a plane projected from a vertical plane including the axis of inclination.

Advantageous Effects of Invention

According to the invention, an easily attachable and detachable culture vessel having a simple structure can be provided, and the cost of the culture vessel can be reduced.

DESCRIPTION OF EMBODIMENTS

Example 1

Figure 1:
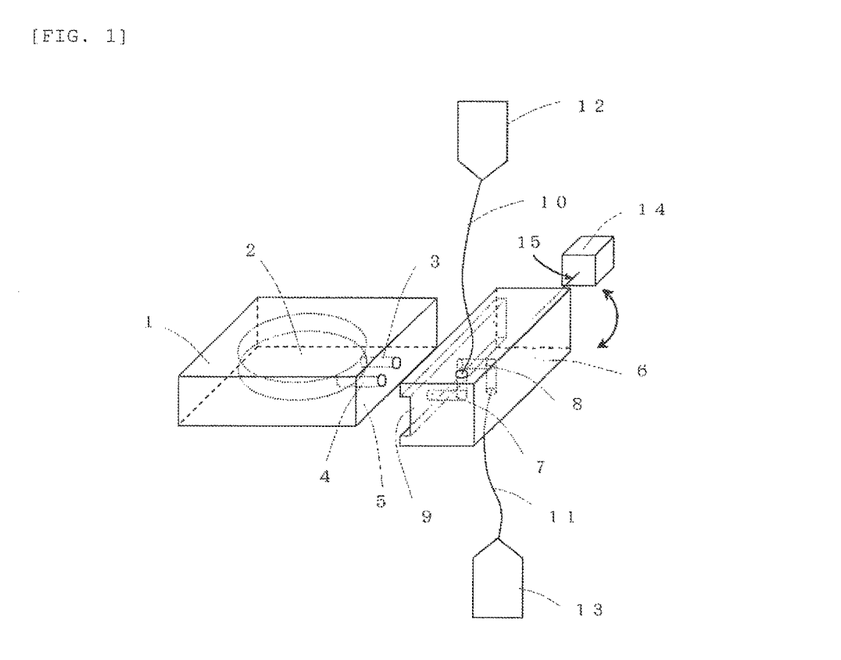
FIG. 1 A schematic explanatory figure of the cell culture device according to the invention.

An Example is explained below using drawings.
FIG. 1 is a schematic explanatory figure of the cell culture device according to the invention. A culture vessel 1 has a structure having a culture chamber 2, an intake flow path 4, a discharge flow path 3 and a connection portion 5. The discharge flow path 3 extends along the normal line to the culture plane of the culture chamber 2 to the connection portion 5. The intake flow path 4 is disposed right next to the discharge flow path 3 and parallel to the discharge flow path 3 and joins the culture chamber 2 and the connection portion 5. The space in the culture chamber 2 is closed when the intake flow path 4 and the discharge flow path 3 are closed. However, a part of the wall of the culture chamber 2 is made of a gas-permeable membrane, which allows gases to be exchanged while maintaining the closed system in the culture chamber 2.

The culture vessel 1 is connected to a supply source of a liquid and a part to which a liquid is discharged, and the connection is preferably through a connection member 6. The connection member 6 has a shape which is paired with that of the culture vessel 1 and has an intake flow path 7, a discharge flow path 8 and a port 9. The intake flow path 7 and the discharge flow path 8 are connected to a supply bag 12 and a liquid waste bag 13 through tubes 10 and 11. The port 9 has a shape which fits the connection portion 5 and enables the culture vessel 1 to be attached and detached from one direction. The connection member may have a plurality of ports and can be connected to a plurality of culture vessels.

A squeeze pump, which is not shown in the drawings, is disposed on the tube 10 or 11, and the tube is squeezed from outside. As a result, a liquid can be sent to the culture vessel.

A plurality of supply bags may be provided and connected to the tube 10 in parallel, and a desired fluid can be sent by selecting the supply bag containing the fluid to be sent with a change valve, which is not shown in the drawings, and then driving the squeeze pump.

To ensure that the culture medium is changed completely, it is preferable to send a new culture medium after the old culture medium is discharged once, and the old culture medium is preferably discharged by being pushed out with air. It is preferable to prepare a bag in which sterilized air is enclosed as a supply bag and send out the air by the switching fluid delivery method above. A HEPA filter may be connected instead of the supply bag containing sterile air. When the size of the filter is reduced, the system can be regarded as a substantially closed system.

Figure 2:
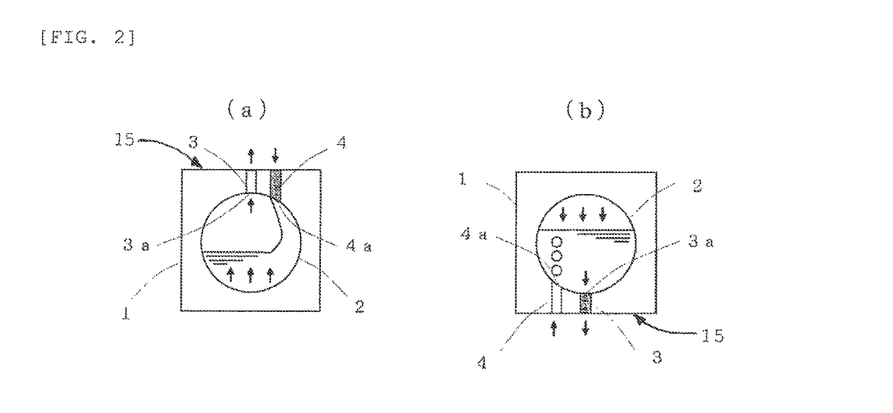
FIG. 2 A figure illustrating how fluids are sent to the culture vessel in the invention.

The cross section of the flow path expands suddenly at the point where the intake flow path 4 of the culture vessel joins with the culture chamber 2. Thus, it is difficult to distribute a liquid to the entire culture chamber just by sending the liquid with the culture vessel in a horizontal position. Accordingly, it is preferable to incline the culture vessel when a liquid is sent. An inclining mechanism 14 is attached to the connection member 6 and can incline the culture vessel when a liquid is sent by rotation around an axis of inclination 15. FIG. 2 shows how this is achieved.

FIG. 2(*a*) shows how a liquid is sent to the culture vessel from the empty state. When a liquid is sent to the culture vessel from the empty state, the culture vessel is inclined in such a manner that a discharge port 3*a* of the culture chamber comes to the top. When a liquid is sent in this state, the liquid which enters from an intake port 4*a* of the culture chamber fills the space from the bottom, and the gas which has been in the culture chamber is pushed up by the liquid and removed from the discharge port 3*a*. Because the discharge port 3*a* is at the top, the air does not remain.

On the contrary, a method for discharging a liquid from the inside for changing the liquid is shown in FIG. 2(*b*). When a liquid is discharged, the culture vessel is inclined in such a manner that the discharge port 3*a* comes to the bottom. When air is sent in this state, the air which enters from the intake port 4*a* moves up because its specific gravity is small, and the liquid which has been in the culture chamber is pushed down by the air and discharged from the discharge port 3*a*. Because the discharge port 3*a* is at the bottom, the liquid can be removed completely.

Figure 3:
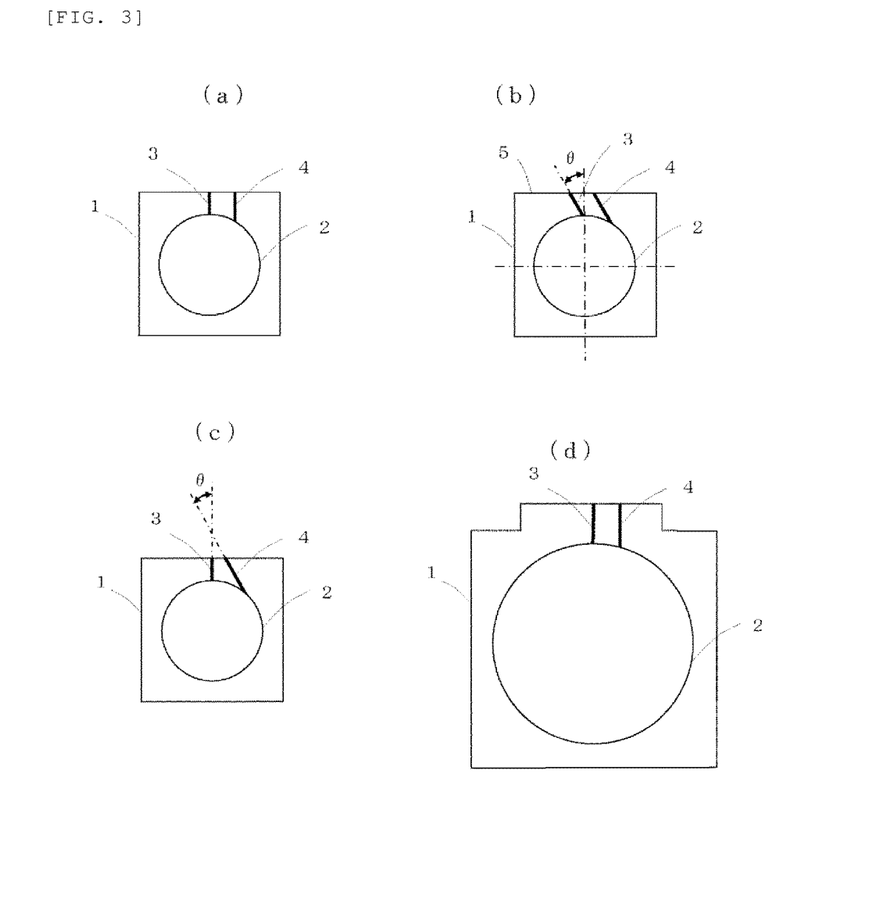
FIG. 3 A figure illustrating modified examples of the culture vessel of the invention.

As long as the discharge port of the culture chamber comes to the top or the bottom when the culture vessel is inclined, the direction of the discharge flow path does not have to be along the normal line to the culture plane. FIG. 3 shows modified examples of the culture vessel of the invention.

Figure (a) shows the example shown in FIGS. 1 and 2, in which the discharge flow path 3 extends along the normal line to the culture plane 2. Figure (b) shows an example in which the discharge flow path 3 is inclined and forms an angle θ with the normal line. By inclining the discharge flow path 3, for example, the inlet of the intake flow path and the outlet of the discharge flow path in the connection portion 5 can be located symmetrically along the central line. Therefore, a symmetrical connection member can be designed. This may result in a reduction in the cost of the connection member.

In order that the discharge port of the culture chamber can come to the top or the bottom when the culture vessel is inclined, the discharge port is provided in the position nearest to the axis of inclination 15. In some cases, no problem arises even when the discharge port does not come to the top or the bottom in the strict sense. Even when the discharge port is slightly shifted from the top or the bottom, a liquid can be sometimes sent without residual air due to the surface tension of the fluid. Also, even when a tiny amount of air remains due to the position of the discharge port, the amount is sometimes so small that it does not cause any problem. The positions of the discharge port in such cases are also regarded as at the top or at the bottom.

The intake flow path does not have to be parallel to the discharge flow path. Figure (c) shows an example in which the intake flow path forms an angle θ with the discharge flow path. When the flow paths form an angle, the production thereof becomes difficult, and thus the cost increases. However, the flow paths may form an angle according to the need. Such a case is advantageous because a liquid can be sent smoothly along the circumferential surface.

The position of the intake port may be any position as long as the discharge port of the culture chamber comes to the top or the bottom when the culture vessel is inclined. Even in the case in which the size of the culture plane is different as shown in figure (d), it is not necessary to change the size of the connection portion and the same connection member can be used, when the distance between the intake port and the discharge port is maintained, rather than changing the position of the intake port similarly to the change in the culture plane size.

The intake port is preferably on a plane projected from a vertical plane including the axis of inclination to the culture plane. That is, the intake port and the discharge port are on the same side when viewed from the vertical plane, and it is not necessary to fold back a flow path. Moreover, it is especially advantageous to the production of the culture vessel that the intake flow path and the discharge flow path are straight and parallel to each other, particularly when the culture vessel is obtained by molding using a resin.

It is desirable that the connection portion and the port each have one face and that the respective flow paths are connected to the faces, so that the flow paths fit each other when the faces are coupled. This structure allows the culture vessel to be attached and detached from one direction, and the attachment and the detachment become easy. In this regard however, a plurality of faces may be provided for the purpose of determining the position or sealing, but the angle formed by the normal lines to the faces should not exceed 180°. In this manner, the culture vessel can be attached and detached from one direction even when a plurality of faces are provided, although it depends also on the positions of the faces.

Example 2

In the following Example, an example of cell cultivation using the culture vessels of the invention is described.

Figure 4:
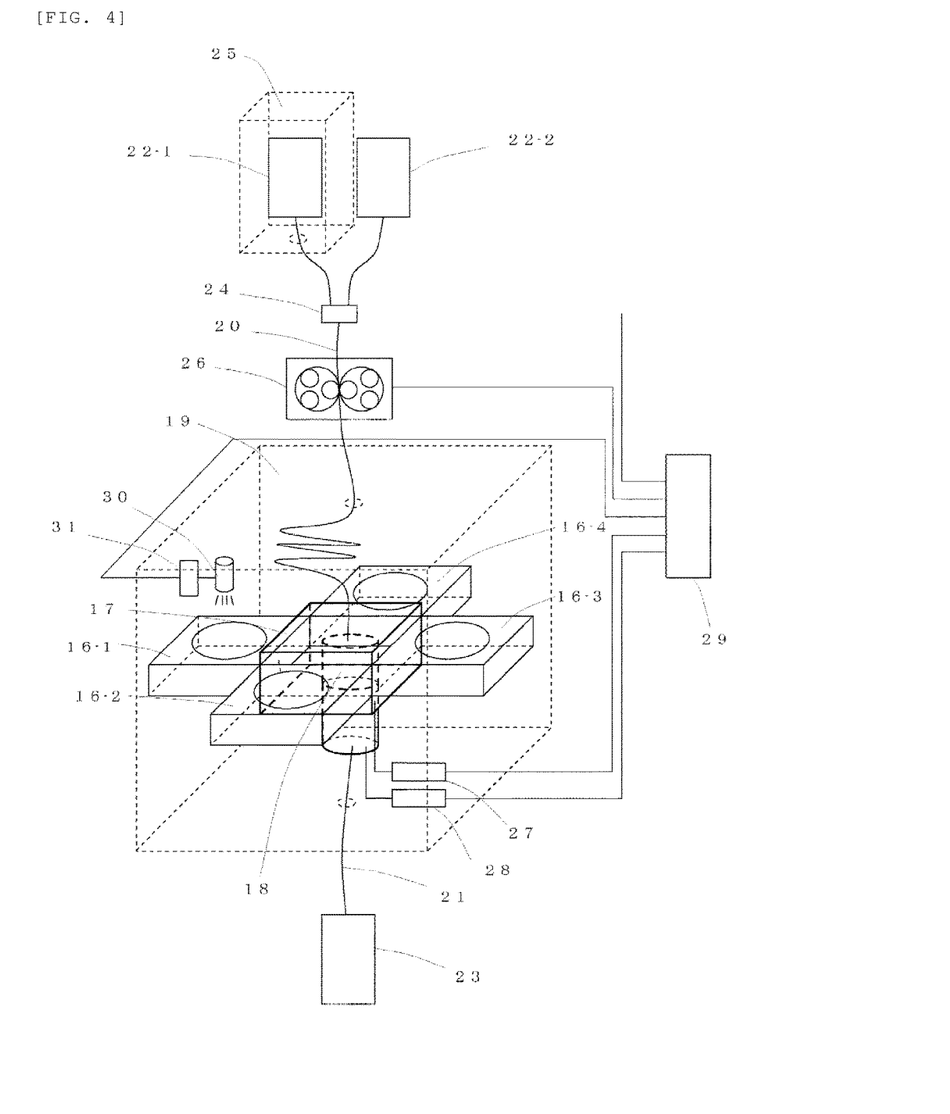
FIG. 4 A figure illustrating the entire structure of a cell culture device.

In FIG. 4, four culture vessels (16-1 to 16-4) are connected to a connection member 17 having four ports. A flow path-switching member 18 is included in the connection member 17 and enables a liquid to be sent to an optional culture vessel. These members including the culture vessels are disposed as a unit in an incubator 19. The environment in the incubator is set according to the type of cultivation. For example, environment settings at a temperature of 37 degrees, a humidity of 95% and a CO2 concentration of 5% are often used.

Tubes 20 and 21 are connected to an upstream part and a downstream part of the connection member 17. The tubes 20 and 21 are connected also to supply bags 22-1 and 22-2 and a recovery bag 23, respectively. A closed culture system is thus formed.

A plurality of supply bags may be provided. A supply bag 22-1 in which a culture medium for change is enclosed and a supply bag 22-2 in which sterile air for discharging an old culture medium is enclosed are provided here. A fluid to be sent from these supply bags can be selected with a change valve 24. The supply bags may be stored in a cooling chamber 25 to keep the quality of the contents.

A squeeze pump 26 is disposed on the tube 20 as a driving source for liquid delivery. The tube 20 is made for example of silicone rubber, and a fluid can be sent by squeezing the flow path due to the elasticity of the tube 20.

The culture plane of a culture vessel spreads widely compared to the intake port. Accordingly, air is apt to remain when a liquid is sent to an empty culture vessel in a horizontal position. It is thus preferable to incline the culture vessel when a liquid is sent so that the air in the culture vessel can be removed completely. The culture vessels described in this Example are configured as a unit with the connection member 17 and thus may be inclined together with the connection member. An inclining mechanism 27 is a mechanism for inclining the connection member.

Figure 5:
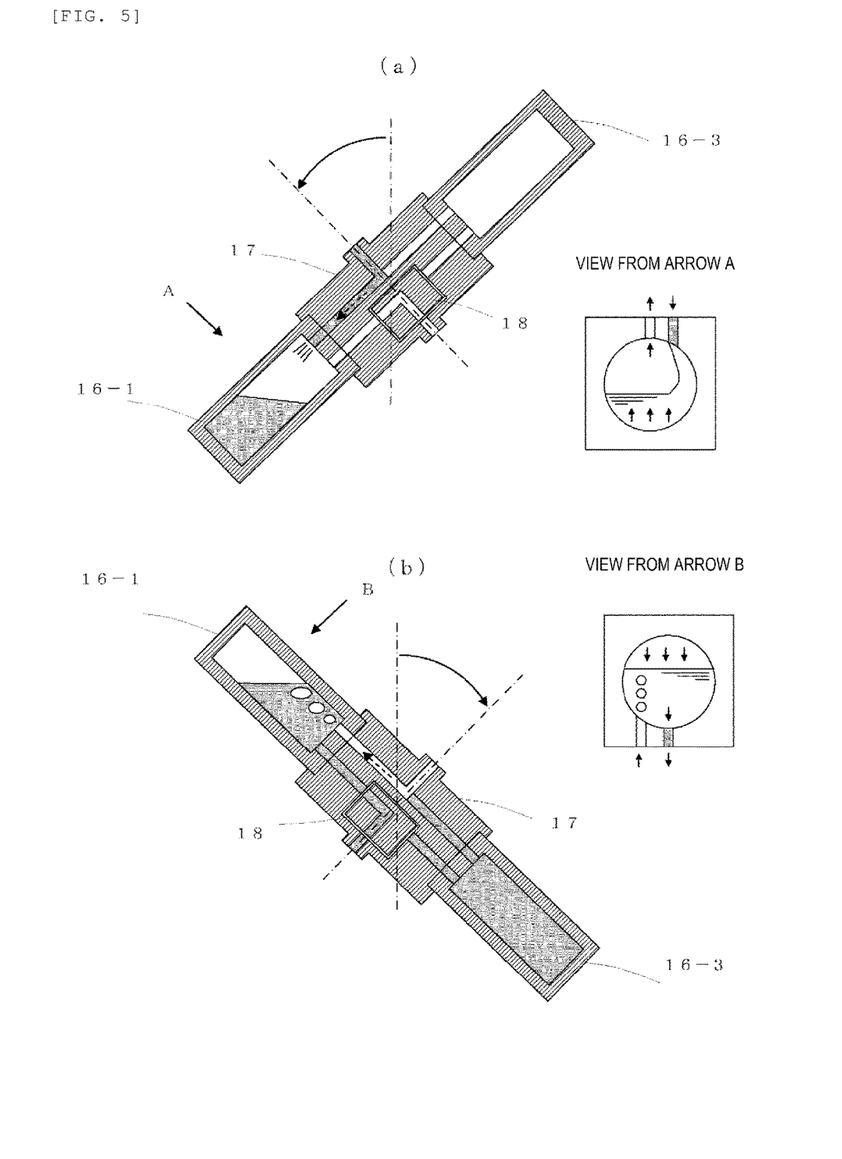
FIG. 5 A figure illustrating how a culture vessel is inclined when fluids are sent.

FIG. 5(*a*) shows how a culture vessel is inclined when a liquid is sent. By inclining the culture vessel downward, in other words, in a manner that the outlet of the culture vessel comes to the top, and sending a liquid in this state, the liquid is sent and fills the space from the bottom and thus can be sent in without residual air. When a liquid in a culture vessel is removed, by inclining the culture vessel upward as shown in (b), in other words, in a manner that the discharge port of the culture vessel comes to the bottom, and sending air in this state, the air sent moves up in the liquid. The liquid is pushed out by the air stored in the upper part, and the liquid can be removed completely.

To switch the flow path-switching member 18, a flow path-switching member-driving mechanism 28 is used. A desired fluid is sent by controlling the change valve 24, the squeeze pump 26, the inclining mechanism 27 and the flow path-switching member-driving mechanism 28 with a controller 29.

Figure 6:
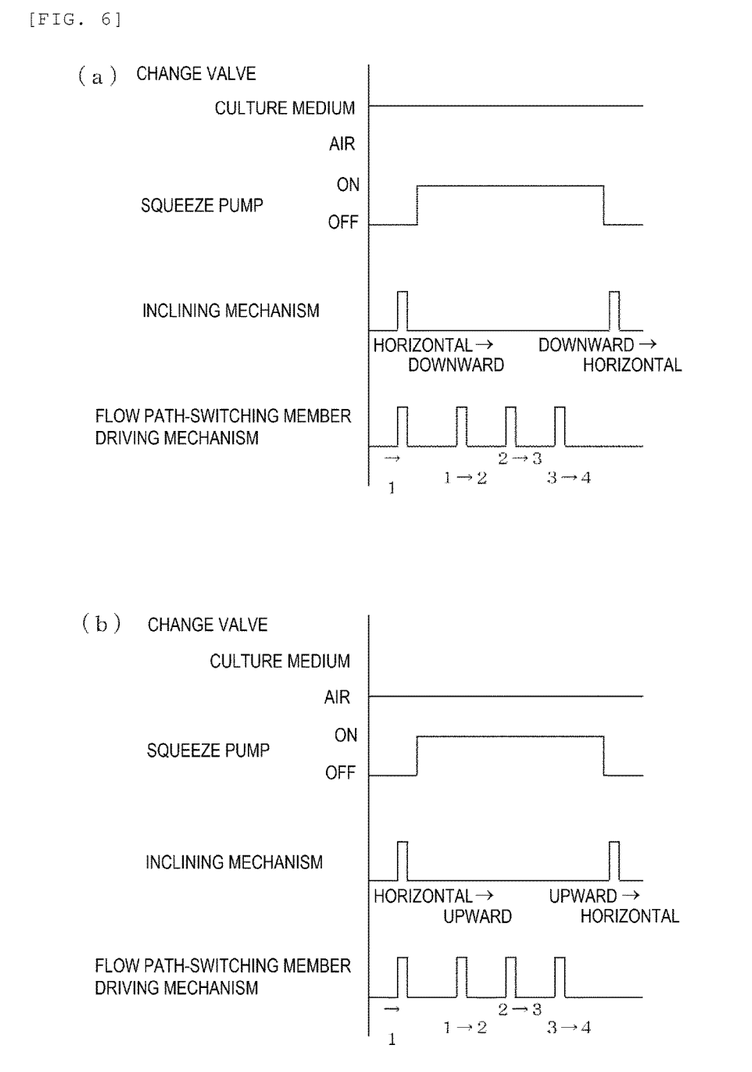
FIG. 6 A figure illustrating control time charts.

A control time chart for sending a culture medium is shown in FIG. 6(*a*). The flow path-switching member-driving mechanism 28 turns the flow path-switching member 18 towards a desired culture vessel, and at the same time, the inclining mechanism inclines the culture vessel together with the connection member downward, in other words, in a manner that the discharge port of the culture vessel comes to the top. The change valve selects the supply bag 22-1 containing a culture medium. When the squeeze pump 26 is driven in this state, the liquid delivery to the desired culture vessel is started. The liquid is sent in this state for a certain period of time. When the culture vessel is filled with the culture medium, the flow path-switching member 18 is driven to select another culture vessel. Then, the inclining mechanism inclines the selected culture vessel, and the liquid delivery is started. By repeating the operations, the culture medium can be supplied to all the four culture vessels. In this regard, for switching the flow paths, it is necessary that the relative positions of the flow path-switching member and the connection member are changed. Thus, the flow path-switching member may be fixed, and the connection member may be driven. With such a structure, switching to a culture vessel to which a liquid is sent becomes possible while the inclination with the inclining mechanism is maintained. FIG. 6 illustrates such a method. The period of the liquid delivery may be a fixed period or may be controlled with a sensor for detecting that the culture vessel is filled with a liquid. When the liquid delivery to all the four culture vessels is completed, the inclining mechanism is driven to return the culture vessels horizontal.

FIG. 6(*b*) shows a control time chart for discharging an old culture medium. Although the supply bag to be selected and the direction of the inclining mechanism are different, the other operations are substantially the same as those for sending the culture medium.

A camera 30 is installed in the incubator so that the state of cultivation in the culture vessels can be observed. When any difference is observed as a result of observation, an alarm can be given or the contents of control can be changed depending on the contents of difference.

A camera-driving mechanism 31 is attached to the camera and is also controlled by the controller 29.

In some cases, not all the ports of the connection member are connected to the culture vessels, and thus a plug which fits the shape of the ports may be provided. The plug requires a function of sealing a liquid only, and thus the plug can be produced at a low price. A necessary number of culture vessels are connected to the connection member, and the plugs may be applied to the remaining ports.

The culture vessels, the connection member and the flow path-switching member are preferably molded resin articles in view of the price. The materials thereof are preferably polystyrene, polypropylene, polycarbonate and the like, which are materials used for general culture vessels.

Depending on the kind of the culture vessel connected, a pumping mechanism for controlling the amount of a liquid to be sent may be provided.

The invention claimed is:

1. A cell culture device having
a culture vessel,
a connection member connected to the culture vessel, and
a pump for supplying a fluid to the culture vessel,
wherein the culture vessel and the connection member are rotatable around an axis of inclination to incline the connection member and the culture vessel by rotation around the axis of inclination,
wherein the culture vessel has a culture chamber, an intake flow path which connects the culture chamber to the connection member via an intake port, and a discharge flow path which connect the culture chamber to the connection member via a discharge port, wherein the discharge port moves between an uppermost position and a lowermost position during rotation of the culture vessel around the axis of inclination, wherein a liquid is supplied to the culture vessel via the intake port while the connection member is inclined with the culture vessel to a side of inclination for supplying the liquid with respect to the axis of inclination with the discharge port substantially at the uppermost position, wherein a gas is supplied to the culture vessel while the connection member is inclined with the culture vessel to a side of inclination for discharging the liquid which is an opposite side to the side of inclination for supplying the liquid with respect to the axis of inclination, so as to discharge the liquid from the culture vessel via the discharge port with the discharge port substantially at the lowermost position, wherein the discharge port is the nearest to the axis of inclination as compared to the intake port which is disposed farther from the axis of inclination than the discharge port, wherein the intake port is in a plane projected from a vertical plane including the axis of inclination, wherein the intake port and the discharge port are disposed on a same side with respect to the vertical plane, and wherein the discharge port is above the axis of inclination at the substantially uppermost position and is below the axis of inclination at the substantially lowermost position.

2. The cell culture device according to claim 1, wherein the intake flow path and the discharge flow path are straight flow paths joining the culture chamber and the connection member.

3. The cell culture device according to claim 1, wherein a plurality of culture vessels can be attached to and detached from the connection member.

4. The cell culture device according to claim 3, wherein the sizes of connection portions of the culture vessels are the same, and the sizes of culture planes of the culture vessels are different.

5. The cell culture device according to claim 3, further comprising a plug for sealing a part in the connection member to which none of the culture vessels is connected.

6. The cell culture device according to claim 1, wherein the culture vessel has one connection portion and can be attached to and detached from the connection member from one direction.

7. The cell culture device according to claim 1, wherein the culture vessel and the connection member are molded resin articles.

8. The cell culture device according to claim 1, further comprising a pumping mechanism for controlling the amount of the liquid to be sent depending on the kind of the culture vessel connected.

9. The cell culture device according to claim 1, wherein the discharge flow path and the intake flow path are straight and parallel to one another.

10. The cell culture device according to claim 1, wherein the discharge flow path and the intake flow path are straight and nonparallel to one another.

11. The cell culture device according to claim 1, wherein the culture chamber has a circular wall and wherein the discharge port and the intake port are provided on the circular wall.

12. The cell culture device according to claim 1, wherein the discharge port at the uppermost position is above all other positions of the discharge port in a full range of inclination of the culture vessel around the axis of inclination, and the discharge port at the lowermost position is below all other positions of the discharge port in the full range of inclination of the culture vessel around the axis of inclination.

13. A cell culture device having
    a culture vessel,
    a connection member connected to the culture vessel, the connection member being movable to be inclined with the culture vessel by rotation around an axis of inclination, and
    a pump for supplying a fluid to the culture vessel,
    wherein the culture vessel has a culture chamber, an intake flow path which connects the culture chamber to the connection member via an intake port, and a discharge flow path which connects culture chamber to the connection member via a discharge port,
    wherein the discharge port moves between an uppermost position and a lowermost position during rotation of the culture vessel around the axis of inclination,
    wherein a liquid is supplied to the culture vessel via the intake port while the connection member is inclined with the culture vessel to a side of inclination for supplying the liquid with respect to the axis of inclination with the discharge port substantially at the uppermost position,
    wherein a gas is supplied to the culture vessel while the connection member is inclined with the culture vessel to a side of inclination for discharging the liquid which is an opposite side to the side of inclination for supplying the liquid with respect to the axis of inclination, so as to discharge the liquid from the culture vessel via the discharge port with the discharge port substantially at the lowermost position,
    wherein the discharge port is the nearest to the axis of inclination as compared to the intake port which is disposed farther from the axis of inclination than the discharge port,
    wherein the intake port is in a plane projected from a vertical plane including the axis of inclination,
    wherein the intake port and the discharge port are disposed on a same side with respect to the vertical plane, and
    wherein the discharge port is above the axis of inclination at the substantially uppermost position and is below the axis of inclination at the substantially lowermost position.

14. The cell culture device according to claim 13, wherein the intake flow path and the discharge flow path are straight flow paths joining the culture chamber and the connection member.

15. The cell culture device according to claim 13, wherein the discharge flow path and the intake flow path are straight and parallel to one another.

16. The cell culture device according to claim 13, wherein the discharge flow path and the intake flow path are straight and nonparallel to one another.

17. The cell culture device according to claim 13, wherein the culture chamber has a circular wall and wherein the discharge port and the intake port are provided on the circular wall at different distances from the connection member.

18. The cell culture device according to claim 13, wherein the discharge port at the uppermost position is above all other positions of the discharge port in a full range of inclination of the culture vessel around the axis of inclination, and the discharge port at the lowermost position is below all other positions of the discharge port in the full range of inclination of the culture vessel around the axis of inclination.

19. A cell culture device having
a culture vessel,
a connection member connected to the culture vessel, and
a pump for supplying a fluid to the culture vessel,
wherein the culture vessel and the connection member are rotatable around an axis of inclination to incline the connection member and the culture vessel by rotation around the axis of inclination,
wherein the culture vessel has a culture chamber, an intake flow path which connects the culture chamber to the connection member via an intake port, and a discharge flow path which connect the culture chamber to the connection member via a discharge port,
wherein the discharge port moves between an uppermost position and a lowermost position during rotation of the culture vessel around the axis of inclination,
wherein a liquid is supplied to the culture vessel via the intake port while the connection member is inclined with the culture vessel to a side of inclination for supplying the liquid with respect to the axis of inclination with the discharge port substantially at the uppermost position,
wherein a gas is supplied to the culture vessel while the connection member is inclined with the culture vessel to a side of inclination for discharging the liquid which is an opposite side to the side of inclination for supplying the liquid with respect to the axis of inclination, so as to discharge the liquid from the culture vessel via the discharge port with the discharge port substantially at the lowermost position,
wherein the discharge port is the nearest to the axis of inclination as compared to the intake port which is disposed farther from the axis of inclination than the discharge port,
wherein the intake port is in a plane projected from a vertical plane including the axis of inclination,
wherein the intake port and the discharge port are disposed on a same side with respect to the vertical plane,
wherein the culture chamber has a circular wall and wherein the discharge port and the intake port are provided on the circular wall, and
wherein the discharge flow path and the intake flow path are straight and nonparallel to one another, the intake flow path being tangential to the circular wall of the culture chamber.

20. The cell culture device according to claim 19, wherein the discharge flow path is radial to the circular wall.

* * * * *